US007312349B2

(12) United States Patent
Rivas-Nass et al.

(10) Patent No.: US 7,312,349 B2
(45) Date of Patent: Dec. 25, 2007

(54) DIENE-BIS-AQUO-RHODIUM(I) COMPLEXES, PROCESS FOR PREPARING THEM AND THEIR USE

(75) Inventors: Andreas Rivas-Nass, Kelkheim Ts. (DE); Gerhard Peter, Freigericht (DE); Jürgen Widmer, Weiterstadt (DE); Ralf Karch, Kleinostheim (DE); Oliver Briel, Alzenau (DE)

(73) Assignee: Umicore AG & Co. KG, Hanau (DE)

( * ) Notice: Subject to any disclaimer, the term of this patent is extended or adjusted under 35 U.S.C. 154(b) by 0 days.

(21) Appl. No.: 10/570,018

(22) PCT Filed: Aug. 10, 2004

(86) PCT No.: PCT/EP2004/008964

§ 371 (c)(1),
(2), (4) Date: Oct. 31, 2006

(87) PCT Pub. No.: WO2005/021153

PCT Pub. Date: Mar. 10, 2005

(65) Prior Publication Data

US 2007/0142654 A1     Jun. 21, 2007

(30) Foreign Application Priority Data

Aug. 28, 2003  (DE)  ................. 103 39 790

(51) Int. Cl.
*C07F 15/00* (2006.01)
*B01J 31/00* (2006.01)
(52) U.S. Cl. ............... 556/136; 502/152; 502/155
(58) Field of Classification Search ......... 556/136; 502/152, 155
See application file for complete search history.

(56) References Cited

U.S. PATENT DOCUMENTS 6,291,606 B1   9/2001   Tang et al.

FOREIGN PATENT DOCUMENTS

WO    WO 02/36261 A2    5/2002

OTHER PUBLICATIONS

Hani El-Amouri, Von et al., "Synthese und katalytische Eigenschaften einseitig offener, zweikerniger $Rf^1$-Komplexe und Struktur von $[Rh_2(CO)_2(CH_3CN)_2\{CH(PPh_2)_3\}](CF_3SO_3)_2$," Angew. Chem. 99, 1987, pp. 1208-1209, Nr. 11, VCH Verlagsgesellschaf mbH, Weinheim, Germany.
Bergbreiter, David E. et al., "Amphoteric, Water-Soluble Polymer-Bound Hydrogenation Catalysts," Tetrahedron Letters, 1997, pp. 3703-3706, vol. 38, No. 21, Elsevier Science Ltd., Great Britain.
Thewissen, D. Harry M. W. et al., "Synthese of $\alpha,\omega$-Bis(disphenylphosphino)alkane and $\alpha,\omega$-Bis(disphenylphosphino)-(poly)ether Ligands and Complexes of Rhodium(I)," Inorganica Chimica Acta, 1985, pp. 143-150, No. 97, Elsevier Sequioa, Switzerland.
Kölle, Ulrich et al., "Olyfin Aqua Complexes of Rhodium(I)," Chem. Ber., 1995, pp. 911-917, No. 128, VCH Verlagsgesellschaf mbH, Weinheim, Germany.
Bats, Jan W., "Low-temperature phase of diaqua(1,5-cyclooctadiene)rhodium(I) trifluoro-methanesulfonate," Acta Cryst., 2004, pp. m85-m87, No. E60, International Union of Crystallography, Great Britain.
Hashmi, A. Stephen K. et al., "On the Enantioselective Rhodium-Catalyzed Enyne Cyclization," Adv. Synth. Catal., 2003, pp. 1237-1241, No. 345, Wiley-VCH Verlag GmbH & Co. KGaA, Weinheim, Germany.
Case, Brenda L. et al., "Reusable, Recoverable, Polymeric Supports: Applications in Homogeneous Catalysis," Chemical Industries, 1998, pp. 403-414, Issue 75, New York, NY.
Motoda, Dai et al., "Phosphane-Free Rhodium Catalyst in an Anionic Micellar System for [4+2] Annulation of Dienynes," Angew. Chem., 2004, pp. 1896-1898, No. 116, Wiley-VCH Verlag GmbH & Co. KGaA, Weinheim, Germany.

*Primary Examiner*—Porfirio Nazario-Gonzalez
(74) *Attorney, Agent, or Firm*—Robert G. Weilacher; Smith, Gambrell & Russell

(57) ABSTRACT

Diene-bis-aquo-rhodium(I) complex of the general formula $[Rh(diene)(H_2O)_2]X$ where diene is a cyclic diene and X is a noncoordinating anion.

23 Claims, No Drawings

DIENE-BIS-AQUO-RHODIUM(I) COMPLEXES, PROCESS FOR PREPARING THEM AND THEIR USE

The present invention relates to diene-bis-aquo-rhodium (I) complexes, a process for preparing them and their use in catalytic reactions and for preparing heterogeneous catalysts.

More than 80% of industrially produced chemicals are produced with the aid of catalytic processes. Catalytic processes are generally more economical arid environmentally friendly than corresponding stoichiometric organic reactions.

In homogeneously catalyzed processes using metal compounds as homogeneous catalysts, the wide range of applications of the catalysts requires a wide range of possible ligand systems. Thus an optimum choice from among a wide variety of ligand systems is necessary to achieve high yields and selectivities in homogeneously catalyzed processes, which at the same time also increases the need for universally usable precursor metal compounds. The need for continual improvement of the catalyst systems and the processes for preparing them is therefore clear.

The majority of the homogeneously catalyzed processes and reactions described in the prior art are concerned with symmetric and asymmetric hydrogenation reactions of unsaturated C—C, C—O, C—S and C—N bonds. Precursor metal compounds for such reactions of great industrial interest are provided, for example, by monomeric and polymeric ruthenium(II) complexes or mononuclear or binuclear rhodium(I)-olefin complexes.

Rhodium(I)-olefin complexes are widely used as, for example, catalysts in symmetric and asymmetric hydrogenation reactions, in hydroformylations, hydrosilylations and coupling reactions. Numerous rhodium(I)-olefin complexes are known in this field of technology, as described, for example, in Houben-Weyl "Methoden der organischen Chemie" (4$^{th}$ Edition, Vol. XIII/9b, "Metallorganische Verbindungen"). All these known complexes have olefinic units which coordinate to the rhodium and stabilize the metal in its respective oxidation state.

Typical olefins present in such complexes are, for example, 1,5-cyclooctadiene (COD), 1,3-cyclooctadiene, norbornadiene (NBD), cyclooctatriene, butadiene, various alkylated and/or substituted butadiene derivatives and ethylene. One of the most frequently used dienes is 1,5-cyclooctadiene (COD).

Since the rhodium in the abovementioned complexes always has the formal oxidation state +1, anionic counterions are always necessarily present. Among these anions, a distinction can be made between those which are coordinated to the rhodium, for example halides, silyl or alkoxy anions, acetates or sulphonates, and those which are not coordinated, for example $PF_6^-$, $BF_4^-$, $B(C_6H_5)_4^-$ and other borate derivatives and also various sulphonates, nitrates and perchlorates.

Apart from purely olefinically coordinated complexes, i.e. complexes in which only olefins or the counterion are coordinated to the rhodium, mixed complexes in which both the olefin and further ligands are coordinated to the rhodium are also known. These further ligands can be, for example, phosphine or phosphite ligands, amines, arsanes or coordinating organic solvents.

Various mixed complexes of this type have been described in the prior art, e.g. complexes in which the rhodium is also doubly coordinated by methanol, ethanol, acetone or acetonitrile as organic solvents in addition to a diene, which is usually COD or NBD, or a phosphine (cf., for example, Osborn et al., Angew. Chemie 99 (1987) 1208-1209). Such complexes which are described in the prior art correspond to a composition represented by one of the general formulas [Rh(diene)$L_2$]X or [Rh(chiral phosphine ligand)(L)$_2$]X, where diene is 1,5-cyclooctadiene (COD) or norbornadiene (NBD), L is acetone, acetonitrile, methanol or ethanol and X is an anion selected from among $BF_4^-$ and $CF_3SO_3^-$.

Some of the compounds described in the prior art have been postulated or identified in solution by means of NMR spectroscopy as intermediates, i.e. in-situ preparations (e.g. in Schrock et al., J. Am. Chem. Soc. 93 (1971) 2397-2407 for L=methanol or acetone), or as precursors of catalysts in hydrogenation reactions. Isolation and separate characterization of these complexes has hitherto not been successful because of their supposedly low stability in the case of, for example, L=acetone.

Bergbreiter et al. (Tetrahedron Letters (1997), 38 (21), 3703-3706, and Chemical Industries (Dekker) (1998), 75 (Catalysis of Organic Reactions), 403-414) describe the use of [Rh(COD)]$CF_3SO_3$. However, the structure and the method of preparing the compound remain undefined and also cannot be deduced from the prior art.

Harry et al. (Inorganica Chimica Acta 97 (1985) 143-150) disclose the preparation and use of [Rh(COD)]$CF_3SO_3$. The structure of the compound described has not been elucidated. The analytical data obtained do not agree with the structure as proposed above. Isolation of a complex of the formula [Rh(COD)(L)$_2$]$CF_3SO_3$ where L=coordinating solvent as a solid is not described; the compounds are merely postulated in solution.

In Chem. Ber. 128 (1995) 911-917, Kölle et al. describe the preparation of various olefin-aquo complexes of rhodium (I). Specifically, the preparation, isolation and use of [Rh(COD)($H_2O$)(p-toluenesulphonate)] is disclosed. Furthermore, Kölle et al. describe the in-situ preparation of a series of complexes of the general formula [Rh(diene)$L_2$]X, where diene is 1,5-cyclooctadiene (COD) or norbornadiene (NBD), L is acetone or water and X is an anion selected from among p-$CH_3(C_6H_4)SO_3^-$ (tosylate, OTs), $CF_3SO_3^-$ or $BF_4^-$. These compounds are prepared using solid silver salts and in solvent mixtures of water and ethanol which are not described in more detail. Some of the compounds mentioned have been postulated as intermediates or, on the basis of NMR-spectroscopic studies, only in solution. In contrast, experimental confirmation of the bisaquo complexes has not been carried out successfully. It was only possible to prepare corresponding complexes with monoolefins, e.g. ethylene, or open-chain 1,3-dienes, e.g. isoprene.

According to Kölle et al., attempts to isolate a complex of the formula [Rh(COD)($H_2O$)$_2$]X failed and led, in the case of OTs$^-$ as anione X, to the complex [Rh(COD)($H_2O$)OTs], i.e. a monoaquo complex. The structure of this complex was able to be confirmed by means of X-ray structure analysis and the structure determined is shown in the following figure:

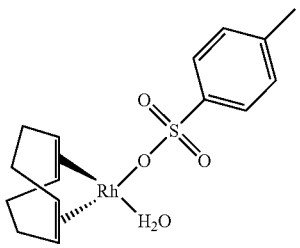

It is an object of the present invention to provide new diene-bis-aquo-rhodium(I) complexes.

The object of the invention is achieved by a novel process for preparing diene-bis-aquo-rhodium(I) complexes which comprises reacting rhodium(I)-olefin compounds with silver salts in an aqueous solvent mixture, characterized in that the silver salt is not added as a solid to the reaction mixture but is instead prepared in solution and added in this form. Furthermore, the invention provides the preparation of diene-bis-aquo-rhodium(I) complexes of the general formula (I):

[Rh(diene)(H$_2$O)$_2$]X       (1)

where diene is a cyclic diene and X is a noncoordinating anion. The present invention also provides for the use of the diene-bis-aquo-rhodium(I) complexes of the invention in catalytic reactions.

As cyclic diene in the general formula (1), it is possible to use any cyclic diene which is able to coordinate to a central metal atom in complexes. According to the invention, cyclic dienes used can be, for example, cyclic hydrocarbons which have from 5 to 12 carbon atoms and two C—C double bonds in the ring. According to the invention, preference is given to cyclic dienes in which the two C—C double bonds are not conjugated. As examples of cyclic dienes which can be used according to the invention, mention may be made of 1,4-cyclohexadiene, 1,4-cycloheptadiene, 1,5-cyclooctadiene (COD), norbornadiene (NBD) and various camphene derivatives. Particularly preferred cyclic dienes for the purposes of the invention are 1,5-cyclooctadiene (COD) and norbornadiene (NBD). Particular preference is given to 1,5-cyclooctadiene (COD).

The radical X in the formula (1) is a noncoordinating anion. According to the invention, X can be any anion which is known in the technical field as being capable of being present in noncoordinated form in metal complexes, in particular in rhodium compounds, particularly preferably in rhodium(I) compounds. As examples of noncoordinating anions which can be used for the purposes of the present invention, mention may be made of $CF_3SO_3^-$, $BF_4^-$, $B(C_6H_5)_4^-$, $B(C_6H_3(CF_3)_2)_4^-$, $B(C_6F_5)_4^-$, $PF_6^-$, $SbF_6^-$ and $ClO_4^-$. Particular preference is given to tetrafluoroborate ($BF_4^-$) and trifluoromethylsulphonate (triflate, $CF_3SO_3^-$.

In a particularly preferred embodiment of the present invention, the diene in the formula (1) is 1,5-cyclooctadiene (COD) and the anion is $BF_4^-$. This complex of the formula [Rh(COD)(H$_2$O)$_2$]BF$_4$ is named 1,5-cyclooctadienebisaquorhodium(1) tetrafluoroborate and has the structure below:

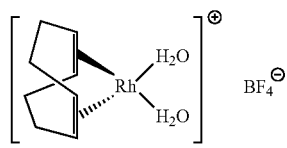

In a further, particularly preferred embodiment of the present invention, the diene in the formula (1) is 1,5-cyclooctadiene (COD) and the anion is $CF_3SO_3^-$. This complex of the formula [Rh(COD)(H$_2$O)$_2$]CF$_3$SO$_3$ is named 1,5-cyclooctadienebisaquorhodium(I) trifluoromethylsulphonate or triflate and has the structure below:

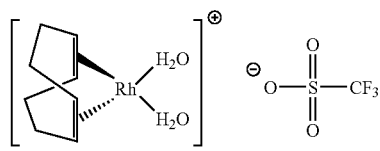

The novel diene-bis-aquo-rhodium(I) complexes described can be prepared either in solution or suspension in any solvent, for example halogen-containing solvents, water, alcohols and ethers, preferably as a solution in water, alcohols such as methanol or ethanol, ethers such as tetrahydrofuran, dioxane and diethyl ether or acetone or in mixtures thereof, or as isolated substances. The diene-bis-aquo-rhodium(I) complexes of the present invention are preferably prepared as solids.

One method known to those skilled in the art for introducing anionic ligands into metal complexes is the transmetallation reaction. It is based on the principle that a precursor compound which is made up of the cation of the desired complex and a replaceable anion is reacted with a suitable metal salt of the anion to be introduced into the complex. In the past, silver salts have been found to be particularly useful as metal salts for introducing various anions into metal complexes, with the appropriate silver salt generally being added as a solid to the reaction mixture.

The process of the present invention for preparing the diene-bis-aquo-rhodium(I) complexes of the invention is characterized in that the appropriate silver salt serving as transmetallation reagent is not added as a solid to the reaction mixture but is instead prepared in solution and added in this form. To prepare a silver salt solution for use according to the present invention, preference is given to reacting a silver-containing starting compound, particularly preferably a basic silver salt such as silver oxide (Ag$_2$O), with a suitable acid in a suitable solvent so as to eliminate water in the case of Ag$_2$O as starting compound and give a solution of the desired silver salt. As suitable acid, the acid corresponding to the noncoordinating anion to be introduced into the diene-bis-aquo-rhodium(I) complex, e.g. trifluoromethanesulphonic acid for preparing a solution of AgCF$_3$SO$_3$, is chosen.

The preparation of the silver salt solution by reacting Ag$_2$O with the appropriate acid is preferably carried out in an aqueous medium. An aqueous medium for the purposes of the invention encompasses water as sole solvent and also all solvent mixtures in which water is the main component of the mixture and is mixed with one or more water-miscible solvents. Examples of such water-miscible solvents are alcohols such as methanol, ethanol, n-propanol, isopropanol, n-butanol and tert-butanol, ethers such as tetrahydrofuran or dioxane, and acetone. Furthermore, an aqueous medium for use according to the invention can comprise water and a water-miscible solvent together with at least one further solvent which is not miscible with water, as long as the solvent mixture forms a homogeneous phase. Examples of such water-immiscible solvents which can be used according to the invention are diethyl ether and methyl tert-butyl ether. The use of water as solvent for preparing the silver salt solution according to the invention is particularly preferred.

The respective acid is preferably used in an excess over the silver oxide for preparing the silver salt solution. This excess of acid can be up to 0.5 molar equivalents and is preferably in the range from 0.01 to 0.15 molar equivalents. The particularly preferred excess of acid over the silver oxide in an individual case can depend on the type of acid used; in particular, the silver oxide should have dissolved completely after the addition is complete. To prepare an $AgBF_4$ solution by the method according to the invention, the acid $HBF_4$ is particularly preferably used in an excess of about 0.03 molar equivalents over the silver oxide, while for the preparation of an $AgCF_3SO_3$ solution according to the invention the particularly preferred excess of $CF_3SO_3H$ is about 0.07 molar equivalents.

Rhodium(I)-olefin compounds which can be used as starting materials in the process of the present invention are in principle all rhodium(I)-olefin compounds which can react with the silver salt solution according to the invention in a transmetallation reaction to form the diene-bis-aquo-rhodium(I) complexes of the invention. As preferred rhodium(I)-olefin compounds for the purposes of the present invention, it is possible to use complexes of the general formula $[Rh(diene)Y]_2$ in which Y is Cl, Br or I and diene is as defined above. A particularly preferred rhodium(I)-olefin compound which can serve as starting compound for the transmetallation reaction is the dimeric rhodium complex $[Rh(COD)Cl]_2$.

As aqueous solvent mixture in which the reaction of the rhodium(I)-olefin compound with the silver salt can be carried out by the process of the invention, it is possible to use all solvent mixtures in which water is present as a constituent. As further constituents of a solvent mixture which can be used according to the invention it is possible to use all water-miscible solvents. The aqueous solvent mixture preferably comprises water together with up to 10% by volume of at least one alcoholic solvent. As preferred alcoholic solvents, it is possible according to the invention to use, in particular, methanol, ethanol, n-propanol, isopropanol, n-butanol and tert-butanol.

In the process of the invention, the reaction of the rhodium(I)-olefin compound with the appropriate silver salt in the aqueous solvent mixture is preferably carried out by adding the previously prepared silver salt solution to a solution or suspension of the rhodium(I)-olefin compound in an aqueous solvent mixture according to the invention. In the addition of the silver salt solution to the solution or suspension of the rhodium(I)-olefin compound in the aqueous solvent mixture, the total amount of silver salt solution can be added all at once or the silver salt solution can be added dropwise over a relatively long period of time, for example up to one hour.

After all of the silver salt solution has been added, the reaction mixture is stirred for a suitable period of time, resulting in a silver salt formed as by-product of the transmetallation reaction being precipitated as a solid. To isolate the desired diene-bis-aquo-rhodium(I) complex, the precipitated solid is subsequently filtered off and washed as often as necessary with a suitable solvent, preferably water. The solvent can be removed from the resulting filtrate in a manner known in the technical field, for example by evaporation on a rotary evaporator, in order to isolate the desired diene-bis-aquo-rhodium(I) complex as a solid.

Both in the preparation of the silver salt solution and in the reaction with the rhodium(I)-olefin compound, the working temperature should, according to the present invention, be selected so that the resulting diene-bis-aquo-rhodium(I) complexes of the present invention do not decompose. For this reason, a temperature of 40° C. should preferably not be exceeded as working temperature as long as the diene-bis-aquo-rhodium(I) complexes of the invention are present in solution. The reactions are particularly preferably carried out at room temperature.

The diene-bis-aquo-rhodium(I) complexes of the invention can be used in catalytic reactions, i.e. both in homogeneous catalysis and in heterogeneous catalysis. The diene-bis-aquo-rhodium(I) complexes of the present invention are particularly suitable for use in asymmetric and symmetric catalytic hydrogenations of double bonds, for example C—C, C—O, C—N or N—N double bonds. Another field of application comprises catalytic hydroformylation reactions and hydrosilylations.

Furthermore, the diene-bis-aquo-rhodium(I) complexes of the invention can be used as precursors for other catalytically active species. The diene-bis-aquo-rhodium(I) complexes of the invention can be used for preparing chirally nonselective, diastereoselective or enantioselective catalytically active species. To generate such catalytically active species, the diene-bis-aquo-rhodium(I) complexes of the invention can be reacted with various achiral and chiral ligands, for example triphenylphosphine, ferrocenylphosphines, alkylphosphines or chiral phosphine ligands, with ligand exchange.

The diene-bis-aquo-rhodium(I) complexes of the invention can also be used for preparing heterogeneous catalysts by any of the processes known in the technical field for immobilizing soluble organic metal complexes. In a particularly preferred embodiment, a diene-bis-aquo-rhodium(I) complex according to the invention can be used as supported or immobilized noble metal catalyst.

EXAMPLES

Example 1

Preparation of $[Rh(COD)(H_2O)_2]BF_4$ 4.63 g of aqueous $HBF_4$ solution (about 50% strength, 26.36 mmol of $HBF_4$, excess over $Ag_2O$: 0.03 molar equivalent) and 10 g of distilled water are weighed into a glass beaker. In addition, 2.96 g of $Ag_2O$ (12.77 mmol) are weighed out onto a paper boat. The $Ag_2O$ is carefully added from the paper boat to the aqueous $HBF_4$ solution over a period of one minute, whereupon the mixture is stirred vigorously. An $AgBF_4$ solution is obtained.

6.0 g of $[Rh(COD)Cl]_2$ (41% of Rh, 2.46 g of Rh, 23.9 mmol) are weighed into a second glass beaker and suspended in 10 g of distilled water and 0.3 g of ethanol (corresponding to about 1.5% by volume of the resulting total solution) by stirring (RCT Basic, setting 4-5) for seven minutes. The entire $AgBF_4$ solution prepared in the first step is poured into the resulting suspension while stirring, resulting in a precipitate being formed. The light-yellow suspension obtained is stirred for about 30 minutes. The precipitate is subsequently filtered off and washed twice with about 5 ml of distilled water. The solution obtained is finally evaporated at 40° C. under reduced pressure on a rotary evaporator. 7.96 g of the title product are isolated (30.3% of Rh, 2.41 g of Rh, 23.4 mmol, yield: 98% based on Rh).

Analysis: $CaH_{16}O_2BF_4Rh$, M=333.9233 g/mol.

$^1$H-NMR ($CDCl_3$, 500 MHz): δ (ppm)=1.57 (s, 4H), 5.46-5.57 (m, 8H).

$^1$H-NMR (d-dioxane, 500 MHz): δ (ppm)=1.73 (dt, J=7.2 Hz, J=8.5 Hz, 4H), 2.50-2.53 (m, 4H), 4.05 (m, 4H).

$^1$H-NMR (MeOD, 500 MHz): δ (ppm)=1.72 (dt, J=6.9 Hz, J=8.5 Hz, 4H), 2.51-2.54 (m, 4H), 4.07 (m, 4H).

IR (KBr, cm$^{-1}$): 3436 (vs), 2939 (m), 2876 (m), 2803 (m), 1639 (m), 1467 (w), 1429 (m), 1325 (w), 1299 (m), 1061 (vs), 958 (m), 794 (m), 521 (m).

% of Rh (measured by ICP=inductively coupled plasma):
% theoretical: 30.82
% actual: 30.30
Elemental analysis:

| % of C, theoretical | 28.77 |
| % of C actual | 28.56 |
| % of H, theoretical | 4.83 |
| % of H actual | 4.98 |

The structure of the complex was confirmed by X-ray crystal structure analysis.

Example 2

Preparation of $[Rh(COD)(H_2O)_2]CF_3SO_3$ 4.92 g of $Ag_2O$ (21.26 mmol) and 10 g of distilled water are weighed into a glass beaker and carefully admixed with 4.1 ml of trifluoromethanesulphonic acid (about 98% pure, 45.40 mmol, excess over $Ag_2O$: 0.07 molar equivalents). A further 10 g of distilled water are added while stirring vigorously. An $AgCF_3SO_3$ solution is obtained.

9.94 g of $[Rh(COD)Cl]_2$ (41% of Rh, 4.08 g of Rh, 39.6 mmol) are weighed into a second glass beaker and suspended in 10 g of distilled water and 0.82 ml of ethanol (corresponding to about 0.5% by volume of the resulting total solution) and 12.7 ml of methanol (corresponding to about 9.5% by volume of the resulting total solution) by stirring (RCT Basic, setting 4-5) for seven minutes. The entire $AgCF_3SO_3$ solution prepared in the first step is poured into the resulting suspension over a period of 30 minutes while stirring, and the $AgCF_3SO_3$ solution is rinsed twice with 5 g each time of distilled water. A precipitate is formed. The light-yellow suspension obtained is stirred for about 30 minutes. The precipitate is subsequently filtered off and washed six times with about 5 ml of distilled water. The solution obtained is finally evaporated at 40° C. under reduced pressure on a rotary evaporator. 15.3 g of the title product are isolated as an orange solid (25.3% of Rh, 3.87 g of Rh, 37.60 mmol, yield: 95% based on Rh).

Analysis: $C_9H_{16}O_5SF_3Rh$, M=396.1879 g/mol.

$^1$H-NMR ($CDCl_3$, 500 MHz): δ (ppm)=1.25 (s, 4H), 2.50-2.53 (m, 4H), 4.09 (m, 4H).

$^1$H-NMR (d-dioxane, 500 MHz): δ (ppm)=1.66 (dt, J=7.2 Hz, J=8.5 Hz, 4H), 2.45-2.47 (m, 4H), 4.02 (m, 4H).

$^1$H-NMR (MeOD, 500 MHz): δ (ppm)=1.63 (dt, J=6.9 Hz, J=8.5 Hz, 4H), 2.38-2.40 (m, 4H), 3.93 (m, 4H).

$^{13}$C-NMR (MeOD, 125 MHz): δ (ppm)=31.57 (d, 4C), 78.81 (d, J=15,2 Hz, 4C), 121,61 (q, J=318.5 Hz).

IR (KBr, cm$^{-1}$): 3415 (vs), 2998 (s), 2924 (s), 2879 (s), 1646 (m), 1433 (w), 1254 (vs), 1178 (vs), 1032 (vs), 969 (m), 643 (s), 582 (m), 518 (m).

% of Rh (measured by ICP=inductively coupled plasma):
% theoretical: 25.97
% actual: 25.30
Elemental analysis:

| % of C, theoretical | 27.28 |
| % of C actual | 26.95 |
| % of H, theoretical | 4.07 |
| % of H actual | 4.3 |
| % of S theoretical | 8.09 |
| % of S actual | 8.33 |

The structure of the complex was confirmed by X-ray crystal structure analysis.

The invention claimed is:

1. Diene-bis-aquo-rhodium(I) complex of the formula:

$$[Rh(diene)(H_2O)_2]X \qquad (1)$$

where diene is a cyclic diene and X is a noncoordinating anion.

2. The diene-bis-aquo-rhodium(I) complex according to claim 1, wherein diene is 1,5-cyclooctadiene (COD) or norbornadiene (NBD).

3. The diene-bis-aquo-rhodium(I) complex according to claim 1, wherein X is a noncoordinating anion selected from the group consisting of $BF_4^-$ and $CF_3SO_3^-$.

4. The diene-bis-aquo-rhodium(I) complex according to claim 2, wherein X is a noncoordinating anion selected from the group consisting of $BF_4^-$ and $CF_3SO_3^-$.

5. The diene-bis-aquo-rhodium(I) complex according to claim 1 having the name 1,5-cyclooctadienebisaquorhodium (I) tetrafluoroborate.

6. The diene-bis-aquo-rhodium(I) complex according to claim 2 having the name 1,5-cyclooctadienebisaquorhodium (I) tetrafluoroborate.

7. Diene-bis-aquo-rhodium(I) complex according to claim 1 having the name 1,5-cyclooctadienebisaquorhodium (I) trifluoromethylsulphonate.

8. Diene-bis-aquo-rhodium(I) complex according to claim 2 having the name 1,5-cyclooctadienebisaquorhodium (I) trifluoromethylsulphonate.

9. The diene-bis-aquo-rhodium(I) complex according to claim 1, wherein the complex is in the form of a solid.

10. Process for preparing a diene-bis-aquo-rhodium(I) complex according to claim 1, which comprises reacting a rhodium(I)-olefin compound with a silver salt in an aqueous solvent mixture as a reaction mixture, wherein the silver salt is prepared in solution and is added to the reaction mixture.

11. The process for preparing a diene-bis-aquo-rhodium (I) complex according to claim 10, wherein the silver salt is prepared in solution by reacting silver oxide ($Ag_2O$) with the acid corresponding to the noncoordinating anion of the diene-bis-aquo-rhodium(I) complex.

12. The process for preparing a diene-bis-aquo-rhodium (I) complex according to claim 10, wherein the acid is used in an excess of up to 0.5 molar equivalents over the silver oxide.

13. The process for preparing a diene-bis-aquo-rhodium (I) complex according to claim 10, wherein the preparation of the silver salt is carried out in an aqueous medium.

14. The process for preparing a diene-bis-aquo-rhodium (I) complex according to claim 11, wherein the preparation of the silver salt is carried out in an aqueous medium.

15. The process for preparing a diene-bis-aquo-rhodium (I) complex according to claim 10, wherein the rhodium(I)-olefin compound is [Rh(COD)Cl]$_2$.

16. The process for preparing a diene-bis-aquo-rhodium (I) complex according to claim 10, wherein the aqueous solvent mixture comprises water together with up to 10% by volume of at least one alcoholic solvent.

17. The process for preparing a diene-bis-aquo-rhodium (I) complex according to claim 11, wherein the aqueous solvent mixture comprises water together with up to 10% by volume of at least one alcoholic solvent.

18. The process for preparing a diene-bis-aquo-rhodium (I) complex according to claim 16, wherein the alcoholic solvent is selected from methanol, ethanol, n-propanol, isopropanol, n-butanol and tert-butanol.

19. In a catalytic reaction, the improvement comprising carrying out said reaction in the presence of diene-bis-aquo-rhodium(I) complex according to claim 1.

20. A method for preparing a heterogeneous catalyst, comprising carrying out said method in the presence of a diene-bis-aquo-rhodium(I) complex according to claim 1.

21. A method for preparing a chirally nonselective, diastereoselective or enantioselective catalytically active species comprising carrying out said method in the presence of a diene-bis-aquo-rhodium(I) complex according to claim 1.

22. The method according to claim 21, wherein the diene-bis-aquo-rhodium(I) complex is reacted with achiral and/or chiral ligands with ligand exchange.

23. The method according to claim 22, wherein the achiral and/or chiral ligands are selected from the group consisting of triphenylphosphine, ferrocenyiphosphine, alkylphosphine and chiral phosphine.

* * * * *